(12) United States Patent
Stegmann et al.

(10) Patent No.: US 8,034,105 B2
(45) Date of Patent: Oct. 11, 2011

(54) OPHTHALMIC IMPLANT FOR TREATMENT OF GLAUCOMA

(75) Inventors: Robert Stegmann, Lynwood Glenn (ZA); Stanley R. Conston, San Carlos, CA (US); David J. Kupiecki, San Francisco, CA (US); John McKenzie, San Carlos, CA (US); Candice D. Pinson, Santa Clara, CA (US); Ronald K. Yamamoto, San Francisco, CA (US)

(73) Assignee: iScience Interventional Corporation, Menlo Park, CA (US)

( * ) Notice: Subject to any disclaimer, the term of this patent is extended or adjusted under 35 U.S.C. 154(b) by 927 days.

(21) Appl. No.: 11/305,306

(22) Filed: Dec. 16, 2005

(65) Prior Publication Data

US 2006/0195187 A1    Aug. 31, 2006

Related U.S. Application Data

(60) Provisional application No. 60/637,368, filed on Dec. 16, 2004.

(51) Int. Cl.
*A61F 2/14* (2006.01)
*A61M 5/00* (2006.01)

(52) U.S. Cl. ............ 623/4.1; 623/5.11; 623/5.12; 604/8

(58) Field of Classification Search .................. 623/4.1, 623/5.11, 5.12
See application file for complete search history.

(56) References Cited

U.S. PATENT DOCUMENTS

| | | | |
|---|---|---|---|
| 5,485,165 A | | 1/1996 | Stegmann |
| 6,102,045 A * | | 8/2000 | Nordquist et al. ............ 128/898 |
| 6,221,078 B1 | | 4/2001 | Bylsma |
| 6,375,642 B1 | | 4/2002 | Grieshaber et al. |
| 6,450,984 B1 * | | 9/2002 | Lynch et al. ...................... 604/8 |
| 6,464,724 B1 | | 10/2002 | Lynch et al. |

(Continued)

FOREIGN PATENT DOCUMENTS

EP    0 898 947    3/1999

(Continued)

OTHER PUBLICATIONS

Int'l Application No. PCT/US2005/045675, Search Report dated Jul. 4, 2006.

(Continued)

*Primary Examiner* — David Isabella
*Assistant Examiner* — Leslie Coburn
(74) *Attorney, Agent, or Firm* — Weaver Austin Villeneuve & Sampson LLP (57) ABSTRACT

A method is provided for increasing the outflow of fluid through Schlemm's canal that is useful for treatment of glaucoma. The implant is placed in Schlemm's canal by use of a flexible delivery instrument attached to the implant. The instrument and implant are positioned within the canal, the implant is released and the distal and proximal ends of the implant are connected to apply sufficient axial tensioning force on the inner wall of the canal to increase fluid permeability. In another embodiment a delivery instrument attached to the implant is positioned in the canal securing one of the distal or proximal ends of the implant within the canal. The implant provides sufficient axial tensioning force on the inner wall of the canal to increase fluid permeability of the inner wall of the canal. The other of the distal or proximal ends may be secured to maintain the tensioning force on the inner wall of the canal.

57 Claims, 7 Drawing Sheets

U.S. PATENT DOCUMENTS

| | | | |
|---|---|---|---|
| 6,494,857 B1 | 12/2002 | Neuhann | |
| 6,533,768 B1 | 3/2003 | Hill | |
| 6,626,858 B2 * | 9/2003 | Lynch et al. | 604/8 |
| 6,638,239 B1 | 10/2003 | Bergheim et al. | |
| 6,827,699 B2 * | 12/2004 | Lynch et al. | 604/8 |
| 6,827,700 B2 * | 12/2004 | Lynch et al. | 604/8 |
| 6,955,656 B2 * | 10/2005 | Bergheim et al. | 604/8 |
| 6,962,573 B1 * | 11/2005 | Wilcox | 604/9 |
| 7,118,547 B2 * | 10/2006 | Dahan | 604/8 |
| 7,135,009 B2 * | 11/2006 | Tu et al. | 604/8 |
| 7,186,232 B1 * | 3/2007 | Smedley et al. | 604/8 |
| 7,220,238 B2 * | 5/2007 | Lynch et al. | 604/8 |
| 7,297,130 B2 * | 11/2007 | Bergheim et al. | 604/8 |
| 2002/0003546 A1 | 1/2002 | Grieshaber et al. | |
| 2002/0013546 A1 | 1/2002 | Grieshaber et al. | |
| 2002/0165478 A1 | 11/2002 | Gharib et al. | |
| 2003/0060748 A1 | 3/2003 | Baikoff | |
| 2004/0024345 A1 * | 2/2004 | Gharib et al. | 604/8 |
| 2004/0024453 A1 * | 2/2004 | Castillejos | 623/4.1 |
| 2004/0127843 A1 | 7/2004 | Tu et al. | |
| 2004/0254520 A1 * | 12/2004 | Porteous et al. | 604/8 |

FOREIGN PATENT DOCUMENTS

| | | |
|---|---|---|
| EP | 1 114 627 | 7/2001 |
| EP | 1310222 | 5/2003 |
| WO | WO 00/07525 | 2/2000 |
| WO | WO 00/64389 | 11/2000 |
| WO | WO 01/97727 | 12/2001 |
| WO | WO 02/36052 | 5/2002 |
| WO | WO 02/074052 | 9/2002 |
| WO | WO 02/080811 | 10/2002 |
| WO | WO 03/015659 | 2/2003 |
| WO | WO 03/045290 | 6/2003 |
| WO | WO 03/045290 A1 | 6/2003 |
| WO | WO 2004/093761 | 11/2004 |

OTHER PUBLICATIONS

Int'l Application No. PCT/US2005/045675, Written Opinion dated Apr. 2005.
Chinese Office Action dated Jul. 18, 2008 for related Chinese Application No. 200580048330.
Cairns, J.E., "Goniospasis: A Method Designed To Relieve Canalicular Blockade In Primary Open-Angle Glaucoma", *Annals of Ophthalmology*, Dec. 1976, pp. 1417-1422.
Grant, M.W., *Arch. Ophthalmol.* 1963; 69:783-801.
Smit, B.A., Johnstone, M.A., *Ophthalmology*, 2002; 109:786-792.
Ellingsen, B.A., Grant, W.M., *Investigative Ophthalmology*, 1972; 11(1): 21-8.
Australian Examination Report dated Jan. 9, 2009 for related Australian Application Serial No. 200704344-1.
Second Office Action dated Mar. 20, 2009 for related Chinese Application No. 200580048330.
Written Opinion dated Oct. 26, 2009 for related Austrian Application No. 200704344-1.
Decision on Rejection dated Jan. 8, 2010 for related Chinese Application No. 200580048330.

* cited by examiner

OPHTHALMIC IMPLANT FOR TREATMENT OF GLAUCOMA

CROSS-REFERENCE TO RELATED APPLICATION

This application claims priority under 35 U.S.C. 119(e) from Provisional U.S. Patent Application Ser. No. 60/637,368, filed Dec. 16, 2004, entitled "OPHTHALMIC IMPLANT FOR TREATMENT OF GLAUCOMA", which is incorporated herein by reference.

BACKGROUND OF INVENTION

Glaucoma is a disease condition of the eye in which increased intraocular pressure (IOP) is created by blockage of the drainage mechanism for the aqueous fluid produced in the anterior portion of the eye. Such aqueous outflow conditions are usually treated by topical drugs in the form of eye drops, but may result in surgical treatment if drug treatment becomes ineffective due to loss of response to the drug or poor patient compliance.

Ophthalmic research has indicated that the greatest resistance to aqueous outflow is in the trabecular meshwork, more specifically, the juxtacanalicular tissue at the inner wall of Schlemm's canal (Grant, M. W., Arch. Ophthalmol. 1963; 69:783-801.) Traditional glaucoma surgery such as trabeculectomy, involves a flap dissection of the eye and the removal of a portion of scleral tissue and of the trabecular meshwork to bypass the normal aqueous outflow pathway and form a direct flow path from the anterior chamber. The aqueous fluid is directed posteriorly under the surgical flap and to a sub-conjunctival lake known as a bleb. Post-surgical complications and bleb management are significant issues with trabeculectomy and similar procedures.

Recently developed surgical treatments for glaucoma involve surgically accessing Schlemm's canal by manner of one or more surgical flaps and subsequently dilating the canal to increase aqueous humor drainage into the natural drainage pathway instead of a bleb. The mechanisms involved in dilating Schlemm's canal to aid aqueous outflow are not fully elucidated. Dilation or expansion of the canal may cause a direct communication between Schlemm's canal and the juxtacanalicular space and may enhance aqueous outflow (Smit, B. A., Johnstone, M. A., Ophthalmology, 2002; 109:786-792). In addition, dilation of the canal may also limit the ability of the inner wall to be distended outward by increased intraocular pressure and press against the outer wall to increase aqueous outflow resistance (Ellingsen, B. A., Grant, W. M., Investigative Ophthalmology, 1972; 11(1): 21-8).

Various approaches and devices for glaucoma surgery involving Schlemm's canal have been described in the prior art. Stegmann, et al. in U.S. Pat. No. 5,486,165 disclose a microcannula designed for delivery of substances to Schlemm's canal during glaucoma surgery. In US 2002/0013546, Grieshaber, et al. disclose a device for holding an expanded lumen of Schlemrnm's canal in a permanently expanded position. Lynch, et al. in U.S. Pat. No. 6,464,724 describe a stent device to expand and maintain the patency of Schlemm's canal. Neuhann in U.S. Pat. No. 6,494,857 describes an implantable longitudinally curved tubular device.

Other methods for improving aqueous humor drainage into Schlemm's canal involve placing a shunt that forms a fluid passage between the anterior chamber and the canal. See Lynch et al. in U.S. Pat. No. 6,450,984, Hill in U.S. Pat. No. 6,533,768 and Gharib et al. in US 20020165478.

Cholinergic drugs such as pilocarpine are the oldest effective medical treatment for glaucoma. These drugs work by a mechanical action by increasing ciliary muscle tone that pulls the scleral spur adjacent to the trabecular meshwork toward a posterior and inward direction. Tension is thereby applied to the trabecular meshwork, opening the intertrabecular spaces, increasing aqueous outflow, and reducing intraocular pressure. The present invention describes an implant that resides within Schlemm's canal of the eye and provides tension to the trabecular meshwork similar to the action of cholinergic or miotic drugs. The use of an implant provides continuous tension and increase in aqueous outflow without re-administration of a drug and without drug side effects. In addition, since the implant applies tension to the trabecular meshwork directly, optical effects to the eye such as fluctuating myopic shift and decreased vision in dim illumination produced by cholinergic drugs are avoided.

While the prior art describes various ways to bypass or to stent the lumen of Schlemm's canal, it does not teach a way to increase aqueous outflow by applying non-drug induced tension to the trabecular meshwork at the inner wall of the canal. The present invention describes a novel approach in surgical treatment of glaucoma by placing an implant in Schlemm's canal that is designed to impart mechanical tension to the interfacing trabecular meshwork on the inner wall of the canal, thereby increasing aqueous outflow and reducing intraocular pressure.

This invention is directed at an ophthalmic implant, which may be directly inserted into Schlemm's canal to improve aqueous outflow through the normal trabeculocanalicular pathway for an extended period of time. The invention is directed to embodiments of and materials for such an implant, and also to tools for placing the implant by minimally invasive methods.

SUMMARY OF THE INVENTION

The invention is directed to an implant for the treatment of glaucoma comprising an elongated element with distal and proximal ends positionable within Schlemm's canal of the eye so as to provide a tensioning force to the inner wall of the canal to thereby increase fluid permeability of the inner wall of the canal. The tensioning force may be axially applied. Axial tensioning is distinguishable from radial tensioning. The former stretches Schlemm's canal on its longitudinal axis. The latter radially stretches the canal. The tensioning force may be provided through a securing element at said one or both ends of the implant and is attachable to a tensioning element providing the tensioning force. In one embodiment, the tensioning element may be a spring which may be accommodated in a protecting housing. In another embodiment, the tensioning element may be a crimping element for securing the implant in a tensioned position. The implant may be provided with an expanded tip or cross-sectional shape to dilate the canal. In some embodiments, the ends of the implant are connected with a tensioning force in the range of about 1 to 11 grams.

The implant may be provided with sufficient mechanical stiffness to impart the tensioning force to the inner wall upon placement within the canal.

In some embodiments, the implant may comprise a helical filament or at least two filaments twisted together in a helical manner or fixed in a parallel manner.

In some embodiments, the implant may comprise a serpentine filament having a circular or ovoid cross-sectional aspect.

In another embodiment, the implant may comprise first regions of a first cross-sectional dimension interspaced with second regions of a second cross-sectional dimension wherein the first cross-sectional dimension is larger than the second cross-sectional dimension. In some embodiments, the first regions comprise beads or cylindrical segments and may freely rotate relative to the second regions.

In another embodiment the implant may comprise filament loops connected to an axial element or connected at alternating ends.

The implant may be provided with a shape to promote flow of aqueous humor from the inner wall of the canal to the collector channels on the outer wall of the canal. In some embodiments, the implant may comprise multiple angular bends resembling a saw-tooth profile, repeating semicircular profiles, a helical filament or a tube with internal channels.

The implant may comprise a metal, a biocompatible polymer and/or a biologically active agent. The biologically active agent may be an anti-thrombogenic agent, anti-microbial agent, anti-inflammatory agent, anti-fibrotic agent, anti-cell proliferative agent or anti-adhesion agent.

The invention is also directed to a tool for insertion of an implant into Schlemm's canal of the eye comprising an implant comprising an elongated element with distal and proximal ends positionable within said canal so as to provide a tensioning force to the inner wall of the canal to thereby increase fluid permeability of the inner wall of the canal, the implant attached to a flexible cannula or guidewire. The tool may further comprise a mechanical element on the cannula for attachment of the implant to the cannula. In some embodiments, the mechanical element may comprise a hole, slot, or an area of increased diameter at a tip of the cannula.

The tool may also comprise a guidance element for locating the tool during placement and advancement within Schlemm's canal. In one embodiment, the guidance element may be a fiber optic beacon. The tool may also comprise an expandable mechanical element for dilating the canal, a lumen for injection of viscous materials, a lubricious coating and/or a rounded tip.

A method is provided for increasing the outflow of fluid through Schlemm's canal that is useful for treatment of glaucoma. The implant is placed in Schlemm's canal by use of a flexible delivery instrument attached to the implant. The method comprises positioning the instrument and implant within the canal, releasing the implant and connecting the distal and proximal ends of the implant to apply sufficient tensioning force on the inner wall of the canal to increase fluid permeability. A method is also provided for increasing the aqueous outflow of fluid through Schlemm's canal in the eye by positioning in the canal a delivery instrument attached to the implant securing one of the distal or proximal ends of the implant within the canal, adjusting the implant to provide sufficient tensioning force on the inner wall of the canal to increase fluid permeability of the inner wall of the canal, and securing the other of the distal or proximal ends within said canal to maintain the tensioning force on the inner wall of the canal.

DESCRIPTION OF THE DRAWINGS

FIGS. 4a and 4b show two embodiments of a filament implant comprising a non-uniform cross-section.

FIGS. 5a and 5b show two embodiments of tensioning filaments arranged in an axial pattern.

FIGS. 6a and 6b show two embodiments of tensioning devices in a configuration of multiple bends designed to place the inner wall of the Schlemm's canal in tension.

FIGS. 10a-10c show delivery instruments with features on the distal tip for attachment of a filament implant.

FIGS. 11a and 11b show an implant comprising a series of round loops slightly overlapping in the manner of a flattened coil spring.

DESCRIPTION OF THE EMBODIMENTS

Figure 1:
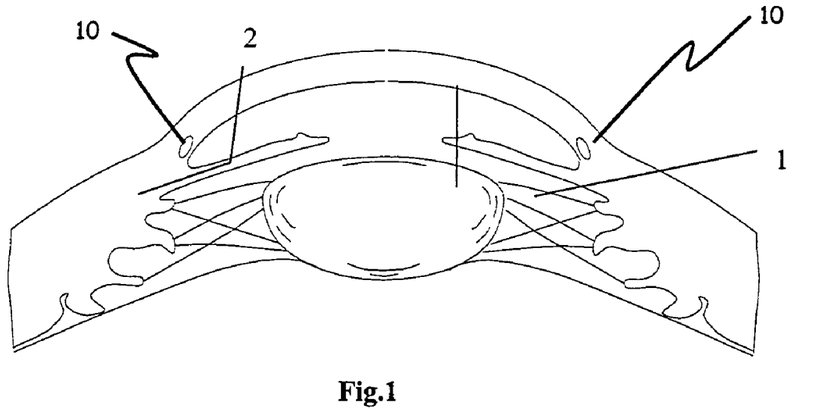
FIG. 1 is a cross-sectional view of the anterior portion of the human eye indicating the location of Schlemm's canal and other relevant structures.
Figure 2:
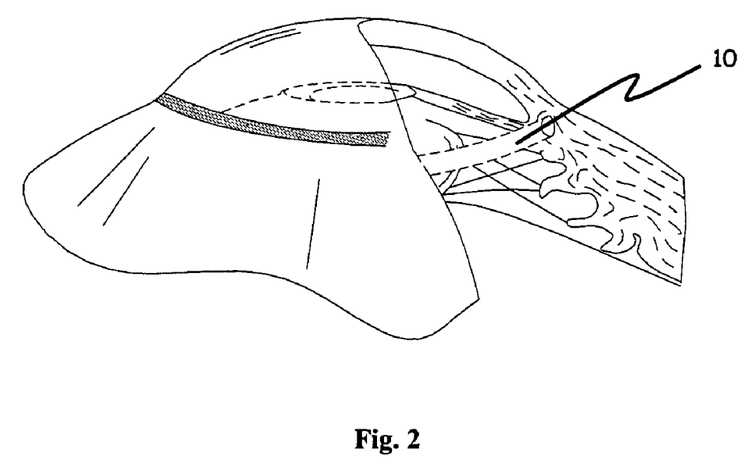
FIG. 2 is a 3-D sectional view indicating the traverse of Schlemm's canal around the limbus.

The invention provides an ophthalmic implant comprising a flexible, elongated element with distal (farthest from the inserting instrument) and proximal (nearest to the inserting instrument) ends, and cross-sectional dimensions less than Schlemm's canal, which may be inserted into the canal and positioned to provide sufficient tension force to the interfacing trabecular meshwork on the inner wall of the canal to improve the outflow of aqueous humor. Referring to FIGS. 1 and 2, Schlemm's canal 10 is a hoop shaped channel in the eye adjacent to the trabecular meshwork. Aqueous humor drains from the anterior chamber through the trabecular meshwork at the inner wall of Schlemm's canal and into the canal. From the canal, the aqueous humor is guided into collector channels and eventually into aqueous veins and the venous system. Schlemm's canal has a radius in the range of approximately 5 to 7 mm and typical ovoid cross-sectional dimensions of 200 microns by 50 microns. Surgical access to Schlemm's canal may be performed by dissection of a scleral flap, as performed in the viscocanalostomy and deep sclerectomy surgical procedures, or by a scleral radial incision. Once surgical access is achieved, the implant is placed into Schlemm's canal and is guided along the circumference of Schlemm's canal. The canal may be pre-dilated by such means as injection of a viscoelastic in order to facilitate the placement of the implant.

Figure 3:
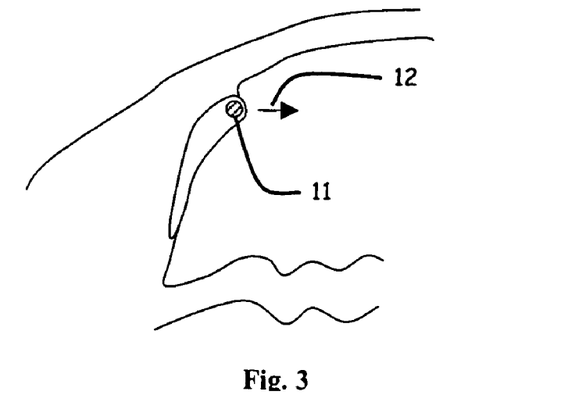
FIG. 3 is a cross-sectional view of a filament implant placed within Schlemm's canal and providing tension on the inner wall (trabecular meshwork) portion of the canal.

Referring to FIG. 3, in one embodiment the distal end of the implant 11 may then be secured to the proximal end and drawn together in a manner to apply tension along the long axis of the implant, and thereby impart a radially inward force 12 to the inner wall of Schlemm's canal. While not intending to be bound by any particular theory, in addition to increasing aqueous outflow through the inner wall of the canal by the application of tension, the radially inward force may also act to limit distension of the inner wall. Distention of the inner wall can decrease the aqueous outflow through the canal due to inner wall contact with the outer wall.

In one embodiment, the implant comprises a filament that is placed within and entirely along the circumference of Schlemm's canal. The proximal and distal ends of the filament are tied together to apply an inward mechanical force on the inner wall of the canal. The filament may comprise elastic or non-elastic material or a combination of elastic and non-elastic materials. The tensioning may be accomplished by use of an elastic implant that has the advantage of applying tension uniformly over the circumference of the canal by stretching the implant before joining the ends. This particular embodiment of the implant applies a mechanical force and tension to the inner wall of the canal and the trabecular meshwork but does not contact or apply mechanical force to the other walls of the canal. The filament may be as small as 10 microns in diameter or as large as the canal, approximately 200 microns. In addition, if the canal is dilated prior to implantation or stretched during implantation, filaments of much larger dimensions, up to 350 microns in diameter may be implanted. The filament may or may not have a lumen or internal or external channels for transport of aqueous humor. The filament may have a uniform or non-uniform cross section to enhance the flow of aqueous in the canal. The filament may comprise any material that is non-toxic and non-inflammatory to the interfacing tissues. Minimal tissue reaction is desired to minimize fibrous tissue formation at the implant-tissue interface, which may compromise outflow of aqueous humor. The implant may also comprise one or more filaments wrapped together or arranged in a parallel manner.

Figure 4A:
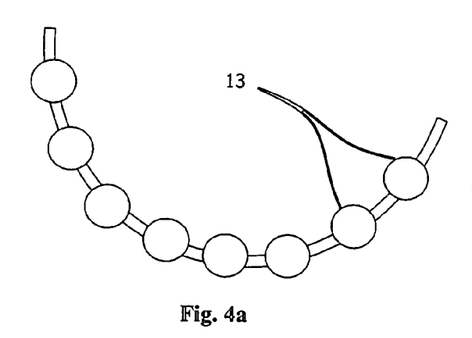
FIG. 4a shows a "bead-on-a-string" format.
Figure 4B:
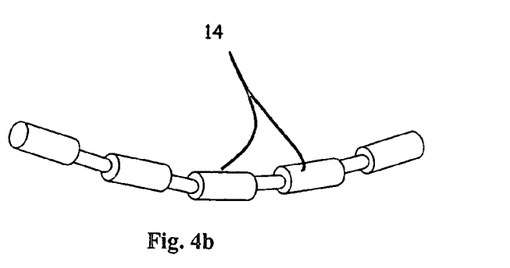
FIG. 4b shows a series of varying diameter cylindrical segments.

In an alternate embodiment, the implant comprises a filament comprising first regions of a first cross-sectional dimension interspaced with second regions of a second cross-sectional dimension such that the first cross-sectional dimension is larger than the second cross-sectional dimension. This non-uniform cross-section, such as relatively uniformly spaced areas of larger cross-section, results in an implant resembling a strand of beads or cylindrical segments, such as shown in the two embodiments of FIG. 4a and FIG. 4b. The beads or areas of larger cross-sectional dimension, 13, 14, may comprise the same material as the smaller filament regions or alternatively may comprise another material. The beads or areas of larger cross-section may be mechanically integral to the smaller filament regions or fabricated such that the beads are threaded over the smaller filament through a channel in the beads. The bead channels and filament dimensions may be sized to allow free rotation of the bead along the axis formed by the channel to minimize mechanical irritation to the interfacing tissues during movement.

Figures 5A, 5B, 6A, 6B:
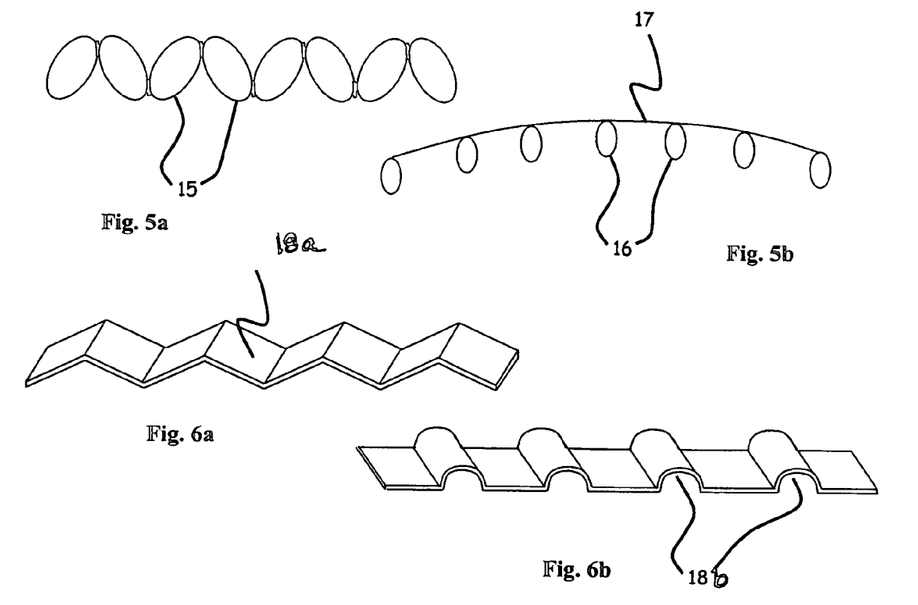
FIG. 5a shows a series of oval loops connected at alternating ends.
FIG. 5b shows a series of loops connected along a backbone.
FIG. 6a shows a device configured in a saw-tooth pattern.
FIG. 6b shows a device configured with serial semi-circular bends.

In another alternate embodiment, the implant may comprise one or more tensioning elements axially aligned. The tensioning elements may be filaments, including wires, having a circular or ovoid cross-sectional aspect. The elements may be connected together, as shown in FIG. 5a, in a looped filament configuration to form a series of oval filament loops 15 attached together alternately at the top and the bottom of the loops, creating a "herringbone" style pattern. Referring to FIG. 5b, the elements 16 may be a series of filament loops connected along an axial backbone element 17. Alternately, referring to FIG. 11, the implant may comprise a series of round loops 31, adjacent to each other or slightly overlapping, in the manner of a flattened coil spring. The elements may be separate components that may be serially placed within the canal. Mechanical force may be applied along the long axis of the implant to apply axial tension only to the inner wall of the canal. In addition, the tensioning elements may be disposed within the canal to place the inner wall of the canal in tension by mechanical force between the inner and outer wall, i.e. the short cross-sectional axis of the canal; or between the anterior and posterior walls of the canal, i.e. the long cross-sectional axis of the canal or a combination thereof. In this fashion, the tensioning elements may be designed to not only provide appropriate tensioning force to the inner wall of the canal, but to also provide a secondary expansion force to separate the walls of the canal or to dilate the canal.

Figure 12:
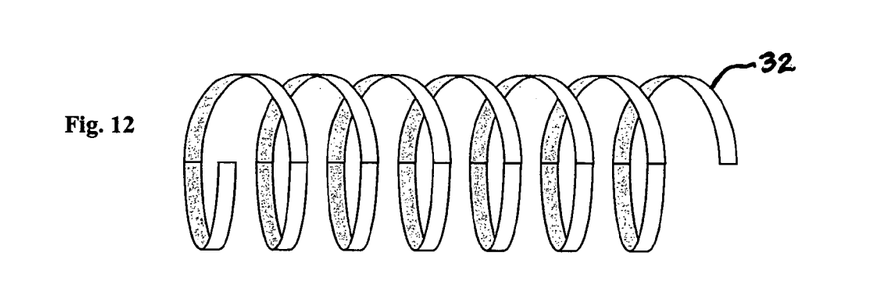
FIG. 12 shows an implant of the invention in the form of a helical filament.
Figure 13:
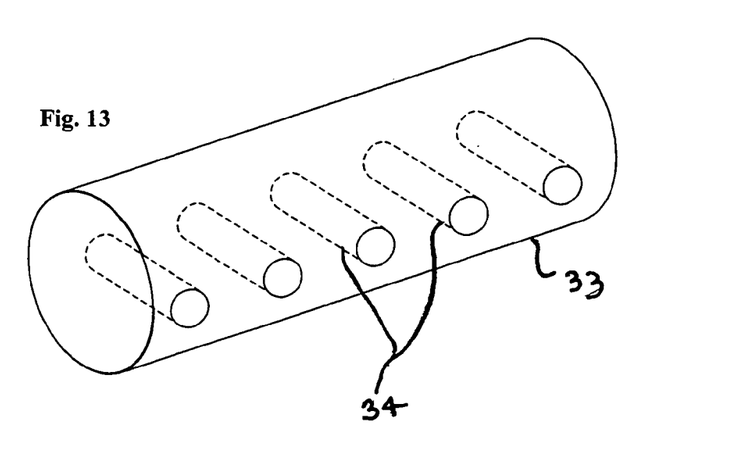
FIG. 13 shows an implant according to the invention that is tubular in shape with internal channels directed from the surface interfacing the inner wall of Schlemm's canal to the surface interfacing the outer wall.

In another alternate embodiment, the implant may comprise a tensioning filament with a shape to promote flow of aqueous humor from the inner wall of Schlemm's canal to the collector channels on the outer wall of the canal. Referring to FIG. 6a, the filament is provided in a configuration with multiple angular bends 18a to resemble a saw-tooth profile. Repeating semi-circular profiles 18b may be provided as shown in FIG. 6b. Referring to FIG. 12, a helical filament 32 may also be used. The implant 33 may also be tubular in shape as exemplified in FIG. 13 with internal channels 34 directed from the surface interfacing the inner wall of the canal to the surface interfacing the outer wall. These embodiments form radially outward flow paths from the inner wall to the outer wall of the canal while applying tension to the inner wall.

The implant is preferred to have sufficient mechanical stiffness to impart tension to the inner wall of Schlemm's canal. The implant may also have sufficient compliance to allow some movement of the inner wall of Schlemm's canal due to normal function of the eye. The implant may also be used in sections to provide the same functionality as a single implant placed along the entire circumference of the canal. For example, instead of completely traversing the circumferential length of the canal to allow connection of the proximal end of the implant to the distal end, the implant may occupy a segment of the circumference. In one embodiment, one end of the implant may be fixed to the tissue near or within the canal and the other extended into the canal and fixed to the tissue at some distance away after imparting sufficient tensioning of the implant between the two ends to provide the desired inward force on the inner wall of the canal. In this fashion, a patient's eye may be treated in segments, for example in the situation where previous eye surgery has rendered a portion of the canal inaccessible to a fully circumferential implant.

The implant may additionally comprise a securement device to facilitate attachment to the other end of the implant or to tissues. The securement device may be attached to one end of the implant or may be a separate component that allows for the attachment and tensioning of both ends of the implant. The securement device may comprise the same material as the filament, a different material or a plurality of materials. For example, a small ring may be fabricated on the proximal end of an implant filament to facilitate tying of the distal end of the filament in a loop. The securement device may comprise an attachment mechanism for the distal end of the implant such that the distal end may be directly attached to the securement device and tensioned with a ratchet type mechanism.

Figure 9:
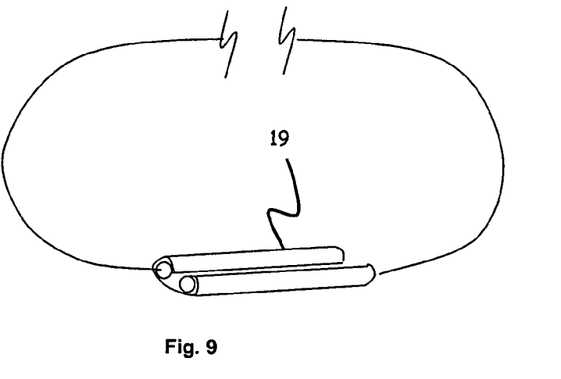
FIG. 9 shows a filament implant with a securement element comprising a crimped coupling to attach the two ends of the filament together under tension.

Alternatively, as shown in FIG. 9, a clamp such as a crimping element 19, which may be a separate component or may be fabricated on one end of the implant, may be used to secure the other end of the implant or to nearby tissue.

Figure 7:
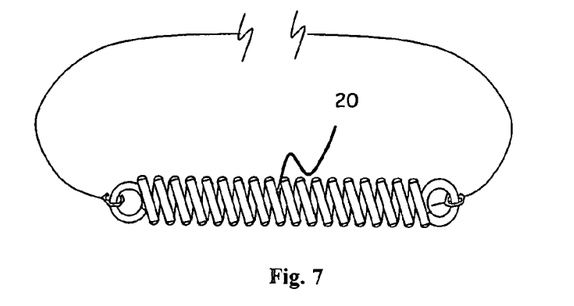
FIG. 7 shows a filament implant with a securement device comprising a spring element to provide tension on the filament in-situ in the eye.
Figure 8A:
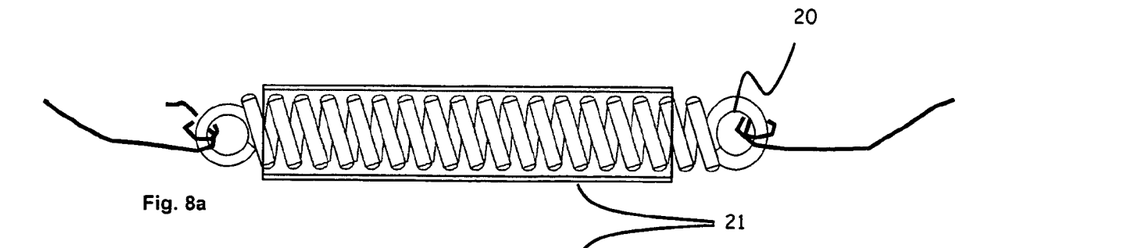
FIGS. 8a ands 8b show a filament implant in expanded and contracted position with a securement device comprising a spring element in a protective housing to provide tension on the filament in-situ in the eye.
Figure 8B:
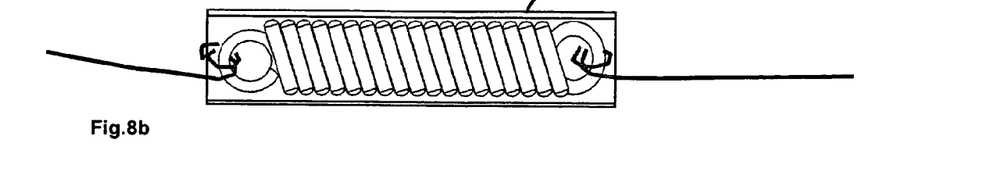

The securement device may comprise a tensioning element such as an elastic material or spring. In FIG. 7 and FIG. 8, a spring 20 is shown which allows the tension on the implant to be adjusted during surgical placement or in a second subsequent procedure after implantation. The spring 20 may also allow for elastic change of the implant length to accommodate tissue motion and thereby minimize motion at the implant-tissue interface and resultant mechanical irritation. The spring may be configured to reside within a protective case or housing 21 to prevent restriction of spring motion by interfacing tissue as well as to protect the tissues from being impinged by the spring element. The spring may also be provided with a feature to measure the tension placed on the implant, such as an indicator of spring extension configured on the outer protective case 21. The spring may be visualized in-situ by gonioscopy through the cornea to evaluate post-operatively the functioning of the implant. Typically, a spring or other elastic tensioning material should provide about 4 to 6 grams force per mm change in length.

In general, the implant is placed in Schlemm's canal by use of a flexible delivery instrument attached to the implant. This may be accomplished by positioning the instrument and implant within the canal, releasing the implant and connecting the distal and proximal ends of the implant to apply sufficient tensioning force on the inner wall of the canal to increase fluid permeability. If the mechanical stiffness of the positioned implant alone is sufficient to impart sufficient tensioning force on the inner wall of the canal, then connecting the ends of the implant may not be necessary. Alternatively, one end of the implant may be anchored to the tissue, then the end may be anchored to the tissue after adjusting the implant to have the proper tension. In this manner the two ends of the implant need not be secured to each other or the implant need not traverse the entire circumferential length of the canal.

The implant is preferably placed in Schlemm's canal by use of a flexible delivery instrument that is used to enter the canal such as described by PCT/US02/37572, incorporated by reference herein. The implant is progressively advanced along Schlemm's canal into the desired location by the delivery instrument, such as a cannula, optionally with prior or concurrent dilation of the canal. The implant may be secured to the delivery instrument and released from the instrument once placed in the desired position within Schlemm's canal or after traversing the circumference of the canal.

Figures 10A, 10B:
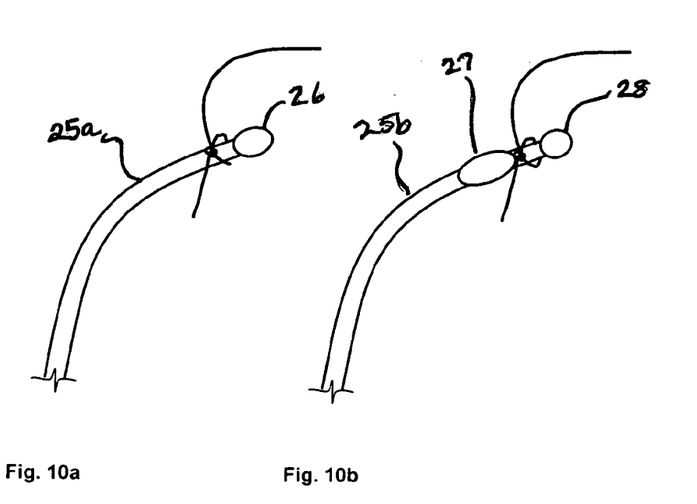
FIG. 10a shows a delivery instrument with a distal tip of larger diameter than the shaft.
FIG. 10b shows a delivery instrument with a larger distal tip, a short segment of shaft and then an enlarged segment of shaft.
Figure 10C:
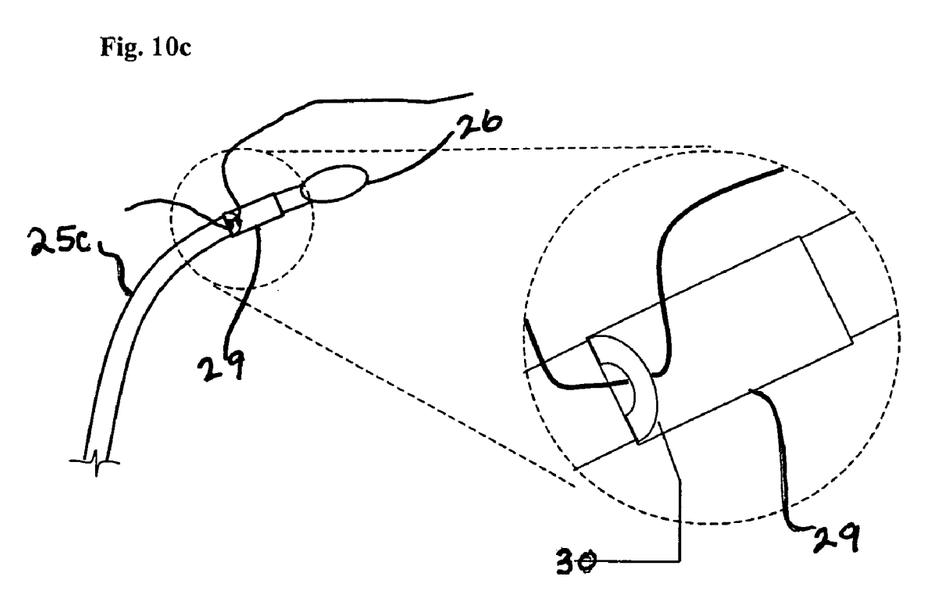
FIG. 10c shows a delivery instrument with a tabbed attachment point as a component of the instrument.
Figure 11A:
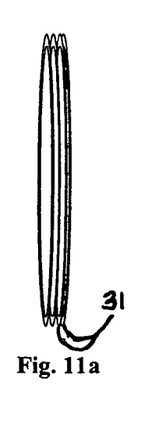
FIG. 11a shows the side view when compressed.
Figure 11B:
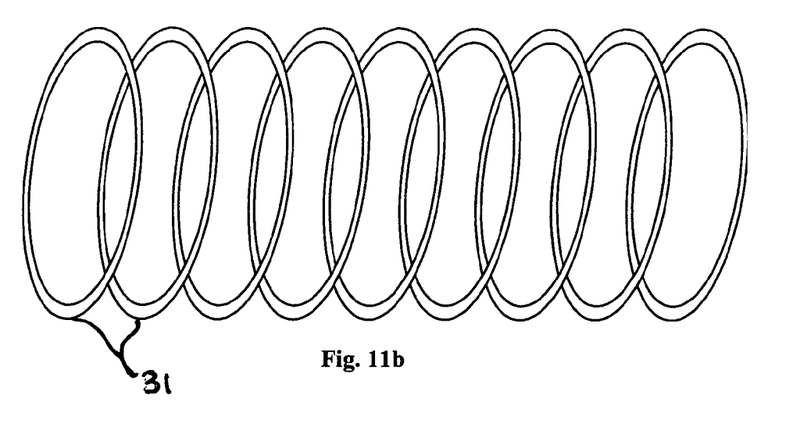

Alternatively, the delivery instrument may be placed in the desired position within the canal, and the implant secured to one end of the instrument, such as a cannula or guidewire, and pulled into the canal during withdrawal of the flexible instrument. As shown in FIGS. 10a-10c delivery instrument 25a, 25b and 25c may have features to aid attachment and release of the implant or its securement device. The instrument may have an increased diameter segment 26 or segments 27, 28 at the distal end to facilitate attachment of one end of the implant. Alternatively, such features may include designs such as an appropriately sized hole or slot at one end of the instrument to insert and attach a portion of the implant. The delivery instrument may have active mechanical element such as collar 29 that accommodates an eyelet tab 30 to attach the implant and/or to release the attached implant once placed appropriately in Schlemm's canal. The delivery instrument may also contain features such as a delivery lumen to allow delivery of a dilating fluid to Schlemm's canal prior to, or concurrent with, placement of the implant. Once in the desired location, mechanical features on the delivery instrument member may be used to release the implant in the proper position.

The delivery instrument may comprise a flexible guidewire or a flexible microcannula designed for 360° cannulation of Schlemm's canal. The delivery instrument will typically be fabricated having a diameter in the range of about 50 to 350 microns to fit within the canal. The flexible delivery instrument may have a curved distal end in a manner to approximate the radius of curvature of Schlemm's canal, typically 5 to 7 mm. The instrument may also comprise a guidance element to effect proper advancement of the distal portion such as described in PCT/US02/37572. Such guidance element may comprise markings or a light transmission device such as a fiber optic beacon at the distal tip of the delivery instrument that allow the surgeon to identify and locate the distal tip through the overlying scleral tissues by either direct visualization or non-invasive imaging during insertion and advancement of the instrument within the canal.

Dilation of Schlemm's canal during advancement of the delivery instrument has been found to facilitate atraumatic placement of the delivery instrument and implant. Dilation may be performed by injection of a high viscosity fluid such as a surgical viscoelastic material to the distal tip of the instrument through a lumen in the instrument. Alternatively, the instrument may comprise expandable elements at the distal tip which may be repeatedly expanded and contracted to dilate the canal during advancement of the device. A rounded distal tip and a lubricious surface treatment may facilitate insertion and progressive advancement of the delivery instrument.

To verify the positioning of the delivery instrument in Schlemm's canal several methods are useful, including use of a fiber-optic beacon tip incorporated into the delivery instrument, direct visual location during surgical cut-down or by external image guidance such as ultrasound imaging or optical coherence tomography. Accurate positioning within the canal may be aided by features of the instrument such as markings to indicate length within the canal, coatings or markers to aid imaging, and markings to indicate rotational alignment. Furthermore, the instrument or implant may incorporate markers to assist in determining its location such as fluorescent or ultrasonically reflective coatings or radio-opaque markers.

In one alternative embodiment, the implant may be placed under direct visualization from the anterior chamber of the eye. The implant secured on a delivery instrument may be placed through a corneal incision into the anterior chamber and through the trabecular meshwork of the eye into Schlemm's canal.

The implant may comprise a variety of materials with suitable biocompatibility and mechanical properties, including metals such as stainless steels, titanium, tungsten, nickel-titanium alloys, cobalt-chrome alloys, biocompatible polymers such as polymethylmethacrylate, polyimide, nylon, polycarbonate, polystyrene, fluorinated polymers, polyetheretherketone, polysulfone, polyethylene, polypropylene, polyesters, polyurethane, polydimethylsiloxane, polybutylene terephthalate, polyethylene terephthalate, parylene, flexible ceramics, carbon, biodegradable materials such as polylactic acid, polyglycolic acid, polyhydroxybuturate, polydioxanone, polytrimethylene carbonate, biopolymers such as silk, collagen, gelatin, glycosoaminoglycans, chitin, chitin derivatives and elastin, and composites of such materials. A filament implant may be circular, oval, rectangular or in a variety of other shapes in cross-section. The implant may be configured from a piece of filament or wire, cut from a length of material with the desired cross-sectional configuration, chemically etched, mechanically or laser machined, extruded or molded.

The implant may also comprise biologically active agents to promote favorable biological response by the interfacing tissues such as the minimization of blood clots (anti-thrombogenic agents), inflammation, infection and fibrosis (anti-fibrotic agents). Such agents include anti-clotting agents such as heparin, TPA, anti-microbial agents such as antibiotics, anti-inflammatory agents such as steroids, anti-adhesion agents such as hyaluronic acid and anti-cell proliferation or anti-fibrotic agents such as rapamycin, 5-fluorouracil, mitomycin, methotrexate or paclitaxol. The biologically active agents may be incorporated into the implant or applied as a coating.

Another function of the implant is that it may serve as a marker and thus be visualized and assessed from the anterior chamber to be safely used as an alignment target for laser treatment of the trabecular meshwork. For example, the implant material of construction and design can allow laser treatment of the adjacent tissue as a means to increase aqueous humor flow in the region of the implant. The laser treatment may be used to increase the permeability of the trabecular meshwork or any fibrotic tissue that may develop in the region of the implant. The laser may be directed to the desired area of treatment through the cornea by non-invasive methods or by the insertion of a fiber optic into the anterior chamber. The implant may have geometry or optically active coatings to aid in the visualization and laser treatment of adjacent tissue.

The following examples are provided to illustrate the invention, but are not intended to limit the invention in any manner.

EXAMPLE 1

Human whole globes were obtained from a qualified tissue bank. The eyes were inflated to approximately 10 mm Hg anterior chamber pressure and placed in a cup-shaped holder. A single flap scleral dissection was performed and Schlemm's canal was exposed, allowing access to the ostia of the canal. A 200 micron diameter ophthalmic microcannula (iTRACK™ microcannula, iScience Surgical Corp.) was used to cannulate the entire canal circumference. The microcannula was designed to provide a means of expanding Schlemm's canal through the injection of viscoelastic materials, and comprised an illuminated beacon tip to provide visual indication of the location of the microcannula when in the canal.

The microcannula was primed with viscoelastic (Healon GV, Advanced Medical Optics, Inc) and inserted into the ostia of the canal. Using a minimal amount of viscoelastic injection to open the canal and provide a lubricious environment, the microcannula was advanced completely around the canal. The distal tip was pulled out of the surgical site a sufficient distance to attach the implant device. A filament of polypropylene of approximately 28 microns diameter (Prolene, Ethicon, Inc.) was tied to the distal end of the microcannula, which was then withdrawn pulling the filament into and around the canal. The filament was removed from the tip of the microcannula and the two ends tied in a surgical knot with tension on the loop, thereby applying tension to the inner wall of Schlemm's canal and the trabecular meshwork. The surgical flap was then closed.

EXAMPLE 2

A human whole globe was prepared similar to Example 1 above. The globe was placed in a room temperature bath of phosphate buffered saline, and a 30 gauge infusion needle placed through the cornea to provide fluid input. The needle was attached to a reservoir containing phosphate buffered saline set at a height of 5.4 inches over the height of the Anterior Chamber to provide a constant pressure infusion of 10 mm Hg. The fluid circuit also comprised a digital flow meter (Sensiron, Inc) to record the flow rates on a PC computer. A stabile baseline flow reading was taken prior to surgical cut-down. Surgical access and implant placement as described in Example 1 above was performed, with the exceptions that a two-flap access was used similar to viscocanalostomy and deep sclerectomy surgery, and the filament was not tied. The ends of the filament were brought out from under the surgical flap and the surgical flap was carefully sealed with cyanoacrylate adhesive without adhering the filament to the tissues. The ends of the filament were tied to the tips of a pair of hemostats. This arrangement allowed for the application and release of tension to the filament loop in the canal by opening and closing the hemostats.

Figure 14:
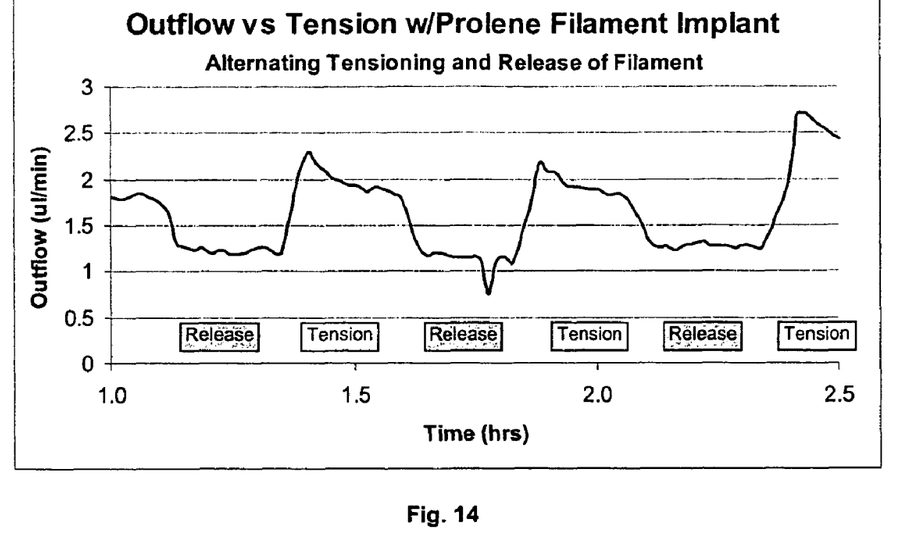
FIG. 14 is a graph of fluid outflow vs applied tension on a prolene filament implant as described according to Example 2.

The globe was returned to the perfusion system and allowed to come to flow equilibrium without tension on the filament. Tension was then applied to the filament by opening the hemostats, and again the flow was allowed to stabilize. Alternate tensioning and release was performed on a 15 minute interval while recording the flow rates. The flow rate changed from a non-tensioned value of 1.22+/−0.05 ul/min to a tensioned value of 1.93+/−0.01 ul/min, an increase of 58%. See FIG. 14.

EXAMPLE 3

Figure 15:
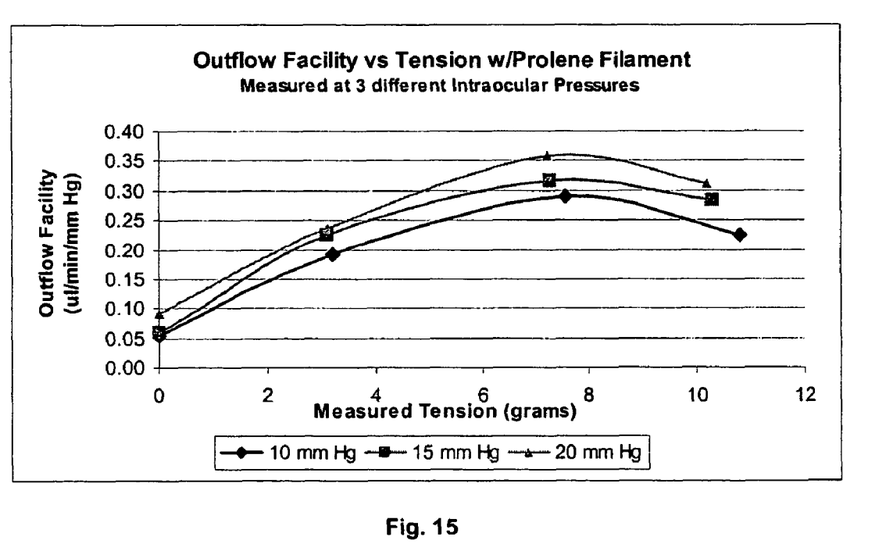
FIG. 15 is a graph of fluid outflow as a function of tension on a prolene filament implant at three different intraocular pressures as described according to Example 3.

In another set of experiments, each end of the 28 micron diameter filament implanted in Schlemm's canal was attached to 30 gram mechanical force gauges (Wagner Instruments) in a fixture such that tension forces could be applied to the filament ends. Outflow measurements were taken at three different intraocular pressure values and with varying tension. The value of the Outflow Facility was calculated by dividing the outflow rate in ul/min by the pressure in mm Hg. The experimental results indicate an optimal value for increasing outflow facility in a tension range of approximately 6-10 grams force along the entire length of the implant long axis, or 0.159 to 0.265 grams per mm arc length of canal for a nominal 12 mm diameter of curvature canal. Outflow was significantly increased in the tension range of 1 to 11 grams force or 0.027 to 0.292 grams force per mm of arc length of the canal for a nominal 12 mm diameter of curvature canal. Further increases in tension led to decreasing outflow facility up to the failure point of the tissues. See FIG. 15.

EXAMPLE 4

In a set of experiments, a tensioning device for the filament was tested. The tensioning device consisted of a micro extension spring element fabricated from nickel-titanium alloy (Nitinol). The spring element was comprised of wire 38 microns diameter, wound in a close packed helix (spring) with an outer diameter of 175 microns and an active coil length of 1.1 mm. The ends of the spring were configured in closed loops at right angles to the axis of the spring, for attachment to the filament implant. The spring was designed to perform in the linear superelastic region of Nitinol to provide a linear spring force in the range 4-6 grams force/mm. The spring element was encased in a thin walled polyimide tube with open ends. The spring was extended to a length of approximately 4 mm and then held in extension with small wire clips resting between a spring loop and the polyimide tube housing. In this manner, the spring could be attached to a filament loop while extended and upon release of the wire clips, the spring would compress thereby placing tension on the loop proportionate to the amount of deflection of the spring. The tension in the filament could be determined by visually examining the amount of spring extension.

Enucleated human whole globes were prepared as in Example 2 above. Comparative experiments were run using the polypropylene filament by itself as the control group and the tensioning device as the test group. In the control group, the filament was tied off in a loop using a slip knot and applying as much tension as could be reasonably achieved with manual techniques. In the test group, the extended spring of the tensioning device was attached to each end of the filament, the slack was taken out of the loop and the release clips removed allowing the spring to retract and tension the filament.

Figure 16:
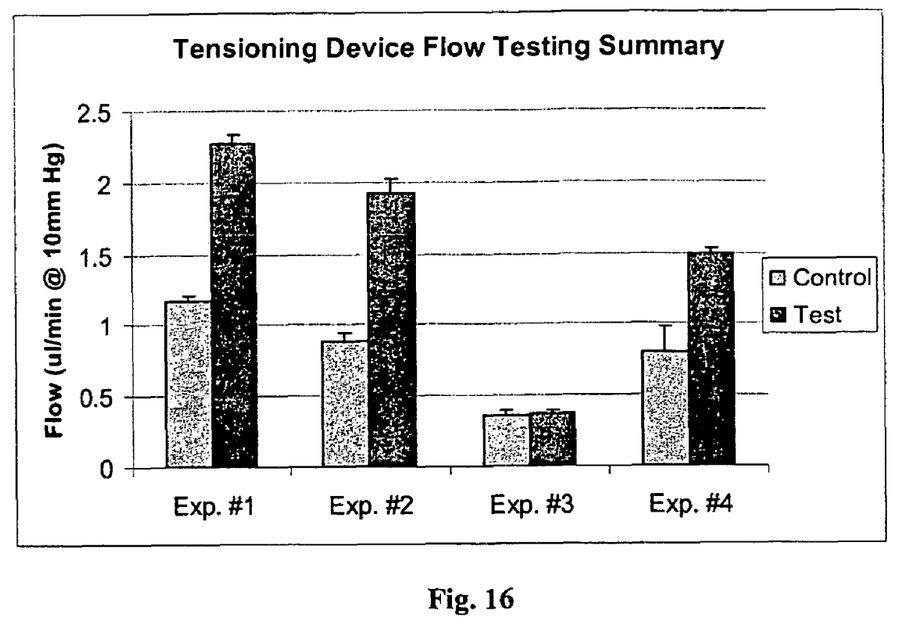
FIG. 16 is a bar graph summarizing outflow in tensioning tests described in Example 4.

The experiment was repeated four times with a significant increase in outflow (approximately twice the control values) seen in 3 of the 4 experiments. The fourth experiment indicated no apparent change. See FIG. 16. Overall, an average increase in outflow of approximately 75% was demonstrated by the use of the filament with a tensioning device.

EXAMPLE 5

An experiment was prepared as in Example 3 above. In this experiment, a 25 micron diameter stainless steel filament was placed into and around the circumference of Schlemm's canal and then attached to the mechanical force gauges to measure the tension applied to the filament and the inner wall of the canal. A high resolution ultrasound imaging system (iVIEW™ imaging system, iScience Surgical Corp) was used to take cross-sectional images of the canal with the implanted filament under different tensions. Images were taken at 0, 5, 10, 15 and 20 grams of tension on the filament. The images indicate an increasing distension of Schlemm's Canal with increasing filament tension. It was observed that Schlemm's canal was visible with an open lumen at all applied tensions, including at filament tensions that demonstrated little or no increase in aqueous outflow or aqueous facility (0, 20 grams applied tension). These results indicate the importance of the appropriate amount of tension applied to the inner wall of Schlemm's canal and the trabecular meshwork to increase aqueous outflow.

The foregoing description of the specific embodiments reveals the general nature of the invention that others can readily modify and/or adapt for various applications of such specific embodiments without departing form the general concept. Therefore, such adaptations and modifications should be and are intended to be comprehended within the meaning and range of equivalents of the disclosed embodiments. It is to be understood that the phraseology or terminology employed herein is for the purpose of description and not of limitation.

What is claimed is:

1. A method for increasing the aqueous outflow of fluid through Schlemm's canal in the eye comprising the steps of
   a) positioning in Schlemm's canal a delivery tool comprising an implant,
   said implant comprising an elongated element with distal and proximal ends positionable within said canal so as to provide a radially inward force to the inner wall of said canal to thereby increase fluid permeability of the inner wall of said canal;
   and a flexible delivery device attached to said implant;
   b) releasing said implant from said flexible delivery device; and
   c) connecting said distal and proximal ends of said implant to each other to apply sufficient tensioning force along the longitudinal axis of said implant to impart a radially inward force on the inner wall of said canal to increase fluid permeability of the inner wall of said canal.

2. A method according to claim 1 comprising the step of withdrawing said delivery device from Schlemm's canal subsequent to releasing said implant in said canal.

3. A method according to claim 1 wherein said implant is provided with sufficient mechanical stiffness to impart said radially inward force to said inner wall upon placement within said canal.

4. A method according to claim 1 wherein said elongated element comprises a helical filament.

5. A method according to claim 1 wherein said implant comprises at least two of said elongated elements twisted together in a helical manner.

6. A method according to claim 1 wherein said implant comprises at least two of said elongated elements fixed in a parallel manner.

7. A method according to claim 1 wherein said elongated element comprises a serpentine filament having a circular cross-sectional aspect.

8. A method according to claim 1 wherein said elongated element comprises a serpentine filament having an ovoid cross-sectional aspect.

9. A method according to claim 7 or 8 wherein said filament comprises a series of loops.

10. A method according to claim 1 wherein said elongated element comprises first regions of a first cross-sectional dimension interspaced with second regions of a second cross-sectional dimension wherein said first cross-sectional dimension is larger than said second cross-sectional dimension.

11. A method according to claim 10 wherein said first regions comprise beads.

12. A method according to claim 10 wherein said first regions comprise cylindrical segments.

13. A method according to claim 10 wherein said first regions freely rotate relative to said second regions.

14. A method according to claim 1 wherein said elongated element comprises filament loops connected to an axial element.

15. A method according to claim 1 wherein said elongated element comprises filament loops connected at alternating ends.

16. A method according to claim 1 wherein said elongated element is provided with a shape comprises multiple angular bends resembling a saw-tooth profile to promote flow of aqueous humor from the inner wall of said canal to the collector channels on the outer wall of said canal.

17. A method according to claim 1 wherein said elongated element is provided with a shape comprises repeating semicircular profiles to promote flow of aqueous humor from the inner wall of said canal to the collector channels on the outer wall of said canal.

18. A method according to claim 1 wherein said elongated element is provided with a shape comprising a helical filament to promote flow of aqueous humor from the inner wall of said canal to the collector channels on the outer wall of said canal.

19. A method according to claim 1 wherein said elongated element is provided with a shape comprising a tube with internal channels to promote flow of aqueous humor from the inner wall of said canal to the collector channels on the outer wall of said canal.

20. A method according to claim 1 wherein said implant is provided with an expanded tip to dilate said canal.

21. A method according to claim 1 wherein said implant comprises a metal.

22. A method according to claim 1 wherein said implant comprises a biocompatible polymer.

23. A method according to claim 1 wherein said implant comprises a biologically active agent.

24. A method according to claim 23 wherein said biologically active agent is selected from the group consisting of an anti-thrombogenic agent, anti-microbial agent, anti-inflammatory agent, anti-fibrotic agent, anti-cell proliferative agent and anti-adhesion agent.

25. A method according to claim 24 wherein said biologically active agent is selected from the group consisting of heparin, tissue plasminogen activator, a steroid, an antimicrobial agent, hyaluronic acid, rapamycin, paclitaxol, 5-fluorouracil, mitomycin and methotrexate.

26. A method according to claim 1 wherein said tensioning force along the longitudinal axis is in the range of about 0.027 to 0.292 grams force per mm arc length of said canal.

27. A method according to claim 26 wherein said tensioning force along the longitudinal axis is in the range of about 0.159 to 0.265 grams force per mm arc length of said canal.

28. A method according to claim 1 wherein said inward force causes distension of said canal.

29. A method according to claim 1 wherein said implant comprises a filament of sufficient length to be placed entirely along the circumference of Schlemm's canal.

30. A method according to claim 29 wherein said implant comprises a non-elastic filament.

31. A method according to claim 29 wherein said filament does not have a lumen.

32. A method according to claim 1 wherein said ends of said implant are attached through a securing element.

33. A method according to claim 32 wherein said securing element is attached to a tensioning element providing said tensioning force.

34. A method for increasing the aqueous outflow of fluid through Schlemm's canal in the eye comprising the steps of
   a) positioning in Schlemm's canal a delivery tool comprising an implant,
   said implant comprising an elongated element with distal and proximal ends positionable within said canal so as to provide a radially inward force to the inner wall of said canal; to thereby increase fluid permeability of the inner wall of said canal;
   and a flexible delivery device attached to said implant;
   b) releasing said implant from said flexible delivery device in said canal;
   c) securing one of said distal or proximal ends within said canal;
   d) adjusting the longitudinal tension of said implant to provide sufficient tensioning force along the longitudinal axis of said implant to impart a radially inward force on the inner wall of said canal to increase fluid permeability of the inner wall of said canal;
   e) securing the other of said distal or proximal ends within said canal to maintain said tensioning force on the inner wall of said canal.

35. A method according to claim 34 comprising the step of withdrawing said delivery device from Schlemm's canal subsequent to securing said implant in said canal.

36. A method according to claim 34 wherein said axial tensioning force is provided to said implant through a securing element at said one or both of said ends, said securing element attachable to a tensioning element providing said tensioning force.

37. A method according to claim 36 wherein said tensioning element comprises a spring.

38. A method according to claim 36 wherein said tensioning element is accommodated in a protecting housing.

39. A method according to claim 36 wherein said tensioning element comprises a crimping element for securing said implant in a tensioned position.

40. A method according to claim 36 wherein said securing element comprises a ring.

41. A method according to claim 36 wherein said tensioning element comprises a spring.

42. A method according to claim 36 wherein said tensioning element comprises an elastic element providing 4 to 6 grams force per mm change in length.

43. A method according to claim 36 wherein said securing element comprises a clamp.

44. A method according to claim 36 wherein said securing element allows adjustment of the length of said implant.

45. A method according to claim 34 wherein said ends are connected with a tensioning force in the range of about 1 to 11 grams.

46. A method according to claim 45 wherein said ends are connected with a tensioning force in the range of about 6 to 10 grams.

47. A method according to claim 34 wherein said inward force causes distension of said canal.

48. A method according to claim 1 or 34 wherein said flexible delivery device comprises a cannula.

49. A method according to claim 1 or 34 wherein said flexible delivery device comprises a guidewire.

50. A method according to claim 1 or 34 wherein said flexible delivery device provides 360° circumferential cannulation of Schlemm's canal.

51. A method according to claim 1 or 34 wherein said flexible delivery device further comprises a mechanical element for attachment of said implant.

52. A method according to claim 51 wherein said mechanical element comprises a hole, slot, or an area of increased diameter at a tip of said flexible delivery device.

53. A method according to claim 1 or 34 wherein said flexible delivery device comprises a guidance element for locating said device during placement and advancement within Schlemm's canal.

54. A method according to claim 53 wherein said guidance element comprises a fiber optic beacon.

55. A method according to claim 1 or 34 wherein said flexible delivery device comprises a lumen for injection of viscous materials.

56. A method according to claim 1 or 34 wherein said flexible delivery device comprises a lubricious coating.

57. A method according to claim 1 or 34 wherein said flexible delivery device comprises a rounded tip.

* * * * *